United States Patent [19]

Eckenhoff et al.

[11] 4,320,758
[45] Mar. 23, 1982

[54] OSMOTICALLY DRIVEN FLUID DISPENSER

[75] Inventors: James B. Eckenhoff; Johan H. Geerke, both of Los Altos; Felix A. Landrau, Milpitas, all of Calif.

[73] Assignee: Alza Corporation, Palo Alto, Calif.

[21] Appl. No.: 214,182

[22] Filed: Dec. 8, 1980

Related U.S. Application Data

[63] Continuation-in-part of Ser. No. 36,815, May 7, 1979, abandoned.

[51] Int. Cl.³ .............................................. A61M 7/00
[52] U.S. Cl. ..................................................... 128/260
[58] Field of Search ................................. 128/213, 260

[56] References Cited

U.S. PATENT DOCUMENTS

| | | | |
|---|---|---|---|
| 3,732,865 | 9/1973 | Higuchi et al. | 128/213 |
| 3,760,805 | 9/1973 | Higuchi | 128/213 |
| 3,987,790 | 10/1976 | Eckenhoff et al. | 128/260 |
| 3,995,631 | 12/1976 | Higuchi et al. | 128/260 |
| 4,034,756 | 7/1977 | Higuchi et al. | 128/213 |

OTHER PUBLICATIONS

Cimmino et al., *Polymer,* 19:1079–1082 (1978).
Union Carbide Corp., "Polyox ®, Water-Soluble Resins are Unique", 1973.

*Primary Examiner*—C. Fred Rosenbaum
*Attorney, Agent, or Firm*—Steven F. Stone; Edward L. Mandell; Paul L. Sabatine

[57] ABSTRACT

An improved version of an osmotically driven miniosmotic pump that is used to administer drug solutions. The basic components of the improved pump are: an inner flexible bag that holds the drug solution; a plug having a recessed inner end that seals the bag opening; a solution filling/discharge port through the plug; a cup-shaped, thermo-formed sleeve that fits partly about the bag and is made from a dispersion of an osmotically effective solute in a water soluble, theroplastic polymer vehicle; a shape-retaining, semipermeable membrane that encapulates the bag-sleeve subassembly; and a flow moderator that is received through the filling/discharge port in the plug.

5 Claims, 3 Drawing Figures

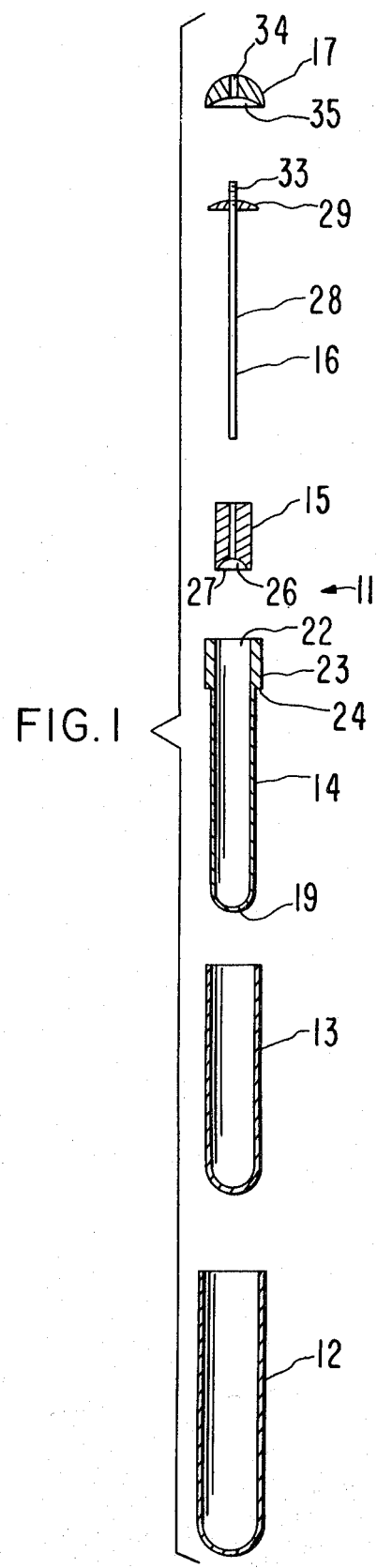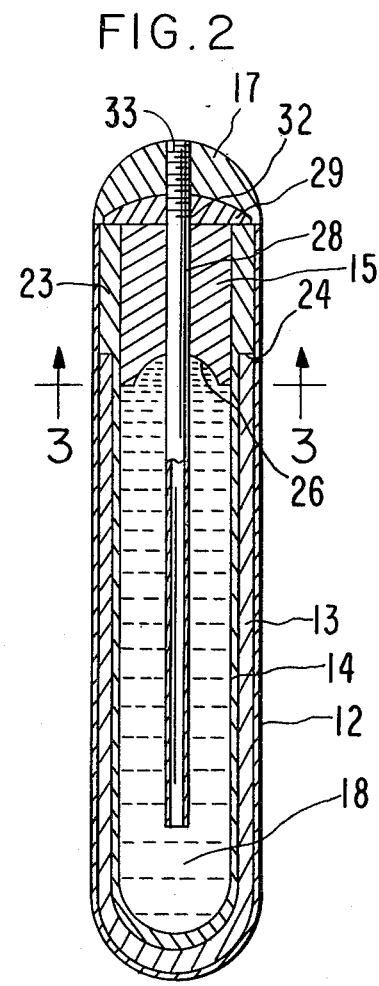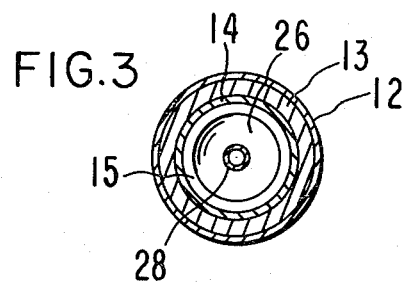

OSMOTICALLY DRIVEN FLUID DISPENSER

CROSS-REFERENCE TO RELATED APPLICATION

This application is a continuation-in-part of U.S. Ser. No. 36,815, filed May 7, 1979 and now abandoned.

BACKGROUND OF THE INVENTION

1. Field of the Invention

The invention relates to improvements and modifications of an osmotically driven fluid dispenser.

2. Description of the Prior Art

The invention is an improvement in the osmotically driven dispensers described in commonly owned U.S. Pat. No. 3,987,790, U.S. Pat. No. 3,995,631 and U.S. Pat. No. 4,034,756. Therefore, these patents are believed to be relevant prior art, particularly the mini-osmotic pump described in these patents. The mini-osmotic pump's components are an inner flexible bag that holds the drug charge, an intermediate layer of an osmotically effective solute composition, such as an inorganic salt, that encapsulates the bag, an outer shape-retaining membrane that is at least in part permeable to water and that encapsulates both the layer of osmotically effective solute composition and the bag, a plug that seals the open end of the bag, and a filling/discharge port that communicates with the interior of the bag.

In operation the bag is filled with drug solution via the filling/discharge port and placed in an aqueous environment, such as a body cavity or within body tissue. Water is imbibed from the environment by the osmotically effective solute through the membrane into the space between the inner flexible bag and the membrane. Since the bag is flexible and the membrane is rigid, the imbibed water squeezes the bag inwardly, thereby displacing drug out the filling/discharge port.

Mini-osmotic pumps of the above described structure and operation perform well but are not beyond being improved. Two shortcomings of the mini-osmotic pump are: (1) the layer of osmotically effective solute is applied by dipping the inner bag into a suspension of an osmotically active solute, which is a highly labor intensive process, and (2) uniformity and reliability of the thickness of the solute layer are difficult to assure in large scale production due to the inherent variability of the dipping process. The first shortcoming affects the ease and cost of production. The second shortcoming affects the average release rate of drug, the constancy of the release rate, and the duration of release. The present invention is directed toward eliminating or reducing both of these shortcomings.

SUMMARY OF THE INVENTION

The invention is an improvement in the composition of the osmotically effective solute layer of the mini-osmotic pump. The improved layer is in the form of a thermoformed sleeve consisting essentially of a dispersion of about 50% to about 90% by weight osmotically effective solute in about 10% to about 50% by weight water soluble, thermoplastic polymer vehicle.

BRIEF DESCRIPTION OF THE DRAWINGS

In the drawings:

FIG. 1 is an elevational, exploded, sectional view of one embodiment of the dispenser of the invention;

FIG. 2 is an enlarged sectional view of the dispenser of FIG. 1; and

FIG. 3 is a sectional view of the dispenser for FIG. 1 taken along line 3—3 of FIG. 2.

Like numerals refer to like parts in the various figures.

DETAILED DESCRIPTION OF THE INVENTION

The drawings illustrate an osmotically driven fluid dispenser, generally designated 11. As shown in FIG. 1, the basic components of dispenser 11 are an outer, shape-retaining semipermeable membrane 12, an intermediate thermoformed sleeve 13 made from a dispersion of an osmotically effective solute in a water soluble, thermoplastic polymer vehicle (matrix), an inner flexible bag 14, a plug 15, a flow moderator 16, and a flow moderator cap 17.

Bag 14 is adapted to contain a fluid composition, such as an active agent composition 18 (FIG. 2) in fluid form. The term "active agent" as used herein means any compound or mixture of compounds that can be dispensed to produce a predetermined beneficial and useful result. Active agents include pesticides, germicides, biocides, algicides, rodenticides, fungicides, insecticides, antioxidants, plant growth promoters, plant growth inhibitors, preservatives, surfactants, disinfectants, sterilization agents, catalysts, chemical reactants, fermentation agents, cosmetics, foods, nutrients, food supplements, drugs, vitamins, sex sterilants, fertility inhibitors, fertility promoters, air purifiers, microorganism attenuators, and other compositions that benefit the environment, surroundings, and habitat, including animals and humans. In the preferred embodiment the active agent is a drug that produces a local or systemic physiologic or pharmacologic response when administered to animals or humans.

In order to be a suitable container for the fluid, bag 14 should be substantially impermeable to the fluid composition and be compatible with the composition. By "compatible", it is meant that the bag should not be corroded, solubilized, or otherwise affected deleteriously by the composition. Additionally, when the composition is a drug, the composition should not be significantly contaminated by the bag, such as by the extraction of leachables from the material forming the bag. Bag 14 may be made from elastomeric compositions that may be formed into thin sheets. The elastomeric properties of the elastomeric composition and the thickness of the bag wall should be such as to cause the bag to readily collapse inwardly when a force is applied to the bag exterior. Such elastomeric compositions are disclosed in commonly owned U.S. Pat. No. 3,760,984 at col. 5, line 40 to col. 7, line 37 and in commonly owned U.S. Pat. No. 3,995,631 at col. 8, lines 14–32 which disclosures are incorporated herein by reference.

Bag 14 is elongated and generally cylindrical and is closed at its end 19 and open at its opposite end 22. Its wall is thickened outwardly at 23 to form a shoulder 24. As seen in FIG. 2 the portion of the exterior of bag 14 below shoulder 24 is encapsulated by sleeve 13 whose wall is approximately as thick as shoulder 24 is wide.

Sleeve 13 is made from a thermoformable osmotically effective solute composition. The components of the composition are an osmotically effective solute and a water soluble, thermoplastic polymer vehicle. The purpose of the solute is to imbibe water from the environment across membrane 12 into the space between the exterior of bag 14 and the inner surface of membrane 12, that is, the space occupied by sleeve 13. The osmotic pressure of the solute when in solution should be significantly greater than the osmotic pressure of the liquid of the environment. In dispensers that are to be ingested by or placed within an animal, the osmotic pressure of the solute solution must exceed the osmotic pressure of body fluids (about 750 kPa). Osmotically effective solutes that may be used in sleeve 13 are disclosed in U.S. Pat. No. 3,760,984 at col. 7, line 38 to col. 8, line 2 and in U.S. Pat. No. 3,995,631 at p. 11, line 65 to col. 12, line 3 and col. 14, lines 20-28, which disclosures are incorporated herein by reference. Sodium chloride is an especially effective osmotic solute in that the osmotic pressure of sodium chloride is sufficiently high to remove the dependence of pumping rate on the osmotic pressure of the surrounding environment. Sodium chloride is efficient in salting out the polymer vehicle so that the influence of binder does not enter into the performance of the dispenser, and the dispenser is less imposing than those containing other salts on the surrounding biological environment.

The polymer vehicle serves to make the osmotically effective composition thermoformable. Depending upon its osmotic pressure in solution it may also contribute to the osmotic effectiveness of the composition. The vehicle functions as a matrix in which the osmotically effective solute is dispersed, and renders the composition flowable upon application of heat and pressure. A preferred vehicle is a mixture of about 40% to about 70% by weight poly(ethylene oxide) having a molecular weight in the range of about 100,000 to about 4,000,000 and about 30% to about 60% by weight poly(ethylene glycol) having a molecular weight in the range of about 1,000 and about 30,000. The cellulose 2-hydroxypropyl ethers sold by Hercules, Inc. under the mark KLUCEL may also be used as the polymer vehicle.

The thermoformability of the composition permits sleeve 13 to be produced by conventional thermoforming techniques such as compression molding, injection molding, or extrusion. Because of this, sleeve 13 may be made as a module in large quantities with a high degree of thickness reproducibility. With sleeve 13 in modular form the assembly of dispenser 11 is simplified. Furthermore, the subassembly composed of bag 14 and sleeve 13 is not as fragile as the solute coated bags of prior versions of the minipump. Thus the subassemblies are less likely to be damaged in the coating process by which membrane 12 is applied to the subassembly.

In addition to the solute and vehicle the osmotically effective solute composition may contain minor amounts of other materials such as fillers, pigments, lubricants, and other conventional additives that facilitate thermoforming.

Sleeve 13 is encapsulated by outer membrane 12. Membrane 12 also covers the exterior of the portion of bag 14 above shoulder 24 and forms a fluid tight seal therewith. At least a part of membrane 12 is permeable to water. Membrane 12 is impermeable to the osmotically effective solute composition. Membrane 12 is also shape-retaining, that is, it is sufficiently rigid to be substantially undeformed by the hydrostatic pressure that is generated in the space between its inner surface and the exterior of bag 14 by the water imbibed by the solute of sleeve 13. The thickness and composition of membrane 12 affects the rate at which water will be imbibed through it by the solute in sleeve 13. Such membranes and compositions that may be used to form them include cellulose acetates, cellulose acetate butyrates, and other shape-retaining semi-permeable membranes including those disclosed in said U.S. Pat. No. 3,760,984 at col. 4, line 53 to col. 5, line 39 and in said U.S. Pat. No. 3,995,631 at col. 7, line 40 to col. 8, line 15, which disclosures are incorporated herein by reference.

Plug 15 fits into the open end 22 of bag 14. Plug 15 is generally cylindrical and is approximately as long as the thickened portion of bag 14 above shoulder 24. The exterior of plug 15 forms a fluid tight seal with the portion of the interior surface of bag 14 with which it is in contact. Plug 15 has an axial, central bore 25 extending completely through it. Bore 25 provides access to the interior of bag 14 for filling bag 14 with active agent composition 18. Bore 25 is also adapted to receive flow moderator 16. Plug 15 has a hemispherically shaped recess 26 in its inner (bottom) end 27. The presence of such a recess or concavity in end 27 reduces the likelihood of entrapping air in bag 14 when filling bag 14 with composition 18. In prior versions of the minipump this plug has been generally cylindrical in shape, its inner end joining the wall of the bag at a 90° angle. During the filling of the bag, the fluid has a natural tendency, due to its high surface tension, to form a curved surface beginning near the top of the wall of the bag and continuing up to the filling/discharge port. This curvature causes an air pocket at the intersection of the wall of the bag and the plug. The improved plug has a hemispherically recessed lower surface, curved to substantially match the arc created by the surface tension of the drug solution during the filling process. This improvement reduces the volume of the dispenser which cannot be filled due to air entrapment from approximately 15% to less than 2% to 3%. Plug 15 may be made from the same materials as are used to make flexible bag 14; however, the dimensions of plug 15 should be such that it is substantially inflexible.

Flow moderator 16 provides the passageway from the interior of bag 14 to the exterior of dispenser 11 by which composition 18 is discharged from dispenser 11. Flow moderator 16 comprises a conduit, in the form of a rigid cylindrical tube 28, and a dome-shaped head 29. Tube 24 and head 29 may be made from suitable plastics or metals. Head 29 has an axial, threaded bore 32 that receives threaded end 33 of tube 28. As shown in FIGS. 1 and 2, end 33 extends outwardly from the spherical surface of head 29 to provide a site for attaching an external catheter tube (not shown) in the event dispenser 11 is to be used to administer composition 18 to a remote location. The outer diameter of tube 28 is approximately the same as the diameter of bore 25 such that tube 28 may be inserted through bore 25 into bag 14 with tube 28 fitting snugly within bore 25 so as to form an essentially fluid tight seal with plug 15. The length of tube 28 is such that it extends into bag 14 to at least about 50% of the elongated dimension of the interior of bag 14, i.e., the distance from the inner side of end 19 to end 27 of plug 15. Preferably tube 28 extends into bag 14 over substantially the entire, but not all of (say 85% to 95%), of said elongated dimension. The inner diameter of tube 28 is correlated to the length of tube 28 such that substantial diffusional flow of composition 18 through tube 28 will not occur. Tube 28 is, in effect, a capillary that provides resistance to the flow of composition 18, thereby reducing or eliminating bulk loss of composition 18, from the outlet port of dispenser 11. Head 29 has a diameter slightly less than the outer diameter of plug 15. As seen in FIG. 2, the flat side of head 29 fits against the top of plug 15.

Dispenser 11 may be filled with fluid 18 via bore 25 of plug 15. For instance, the needle of a fluid loaded syringe may be inserted through bore 25 and the syringe's contents discharged into bag 14. To insure that a predetermined fluid pumping rate is achieved, it is desirable to completely fill bag 14 with fluid 18. After the bag is filled, tube 28 of flow moderator 16 is inserted through bore 25 to the position shown in FIG. 2. As described above, tube 28 functions as a capillary and inhibits loss of fluid 18 from the dispenser even though it is subjected to substantial movement or tipped upside down. Dispenser 11 operates in the following manner. Once placed in aqueous enviroment, such as within a body cavity or within body tissue, water from the enviroment is imbibed by the solute of sleeve 13 through membrane 12 at a rate determined by the osmotic activity of the solute, and the osmotic reflection coefficient, composition, thickness, and area of membrane 12. The imbibed water causes the volume of the space between the inner surface of membrane 12 and the exterior of bag 14 (the space initially occupied by sleeve 13) to increase. And since membrane 12 is shape-retaining, the imbibed water generates hydraulic pressure on the exterior of bag 14 causing bag 14 to be squeezed inwardly. This squeezing forces fluid 18 through tube 28 and out of the dispenser. As indicated, fluid 18 may be an active agent composition. In such instances the dispenser 11 will, of course, discharge active agent directly. Alternatively, fluid 18 may be inert and the dispenser may be used simply as a displacement pump. In this alternative the dispenser will, of course, have to be suitably interconnected by well known means to a reseroir of the fluid (active agent) to be discharged, such that the inert fluid displaces the fluid from the reservoir in a predetermined regimen to the desired administration site. Such alternatives are particularly attractive in instances in which the fluid to be discharged is incompatible with bag 14.

Flow moderator cap 17 may be used to cover protruding end 33 of tube 29 when dispenser 11 is used without an external catheter tube connection. Cap 17 is crescent-shaped and has an axial threaded bore 34 that receives end 33 of tube 29. The curvature of its concave underside 35 matches the convexity of the top surface of head 29 so that the former fits tightly against the latter (FIG. 2). The outer diameter of cap 17 is the same as the outer diameter of membrane 12. Thus the hemispherical exterior of cap 17 provides a smooth blunt surface that aligns with the exterior surface of membrane 12.

The components of dispenser 11 may be made and assembled as follows. Bag 14 and sleeve 13 are thermoformed, such as by injection molding, by known techniques. The bag-sleeve subassembly may be made using solvent or adhesive bonding, depending on the material involved. If bag 14 and sleeve 13 are capable of being solvent bonded, bag 14 is dipped in the mutual solvent and inserted into sleeve 13. When the subassembly is put together by adhesive bonding, bag 14 is dipped into an appropriate adhesive and then inserted into sleeve 13. Membrane 12 may be applied to the bag-sleeve subassembly by dipping it in a solution of membrane material as taught in U.S. Pat. No. 3,987,790 at col. 4, line 63 or membrane 12 may be coated onto the subassembly using conventional coating equipment and techniques such as pan coating and fluidized spray coating.

The following example is intended to further illustrate the above described dispenser and its manufacture. This example is not intended to limit the invention in any way.

EXAMPLE

Cylindrical flexible bags (2.50 cm long, 4.01 mm I.D. and 4.62 mm O.D.) were injection molded at 176° C., $3.5 \times 10^3$ kPa, from an elastomeric styrene-butadiene copolymer (sold under the trade designation, Kraton 2104).

Osmotic sleeves were prepared for each dispenser as follows. The components (64.5 wt% NaCl, 20 w% poly[ethylene oxide], molecular wt 600,000, 15 wt% poly[ethylene glycol] of molecular weight 20,000 and 0.5 wt% colloidal $SiO_2$, sold under the trade name [Cabosil] were bulk blended in a Hobart mixer for 20 minutes at low speed. The homogenous powder blend was pressed into 0.6 cm tablets capable of being gravity fed into Arborg injection molding equipment. The osmotic sleeves (2.21 cm long, 4.87 mm I.D., and 5.89 mm O.D.) were formed from the tablets by injection molding at 149° C. $6.5 \times 10^3$ kPa.

Cylindrical plugs of the above described styrene-butadiene copolymer were injection molded. The plugs were 0.5 cm long, had a 4.1 mm O.D., their lower surfaces were recessed hemispherically to a depth of 1.37 mm, and had a central axial bore 0.76 mm in diameter through the length of the plug.

The cylindrical flexible bags were dipped into a 15 wt% cyclohexane solution of the styrene-butadiene copolymer mentioned above and were inserted into the osmotic sleeve. The arcuate surfaces of the plugs were coated with a glue bead of 15 wt% cyclohexane solution of the copolymer and a plug was inserted into the open end of each of the bags. A 22 gauge needle was inserted through the bore of each plug and the plugged bags were placed in an oven at 40° C. for 2 hours.

An outer semipermeable membrane was applied to the dispensers by coating with a Wurster coater. The membrane was a 4 wt% methylene chloride solution of cellulose acetate butyrate (sold under the designation Eastman Kodak 381-2). The coating was applied to a thickness of 0.38 mm. The dispensers were then oven-dried at 55° C. for about 5–10 days.

Flow moderators were prepared for each dispenser as follows. Twenty-one gauge needle stock was cut into 2.36 cm lengths. Each length of tubing was circumferentially grooved with 15 grooves, equally spaced 0.3 mm apart along one end of the tube, such that a 4.3 mm distance beginning at one end of the tube is grooved. Caps were insert molded around the grooved portion of the tube 3 mm from the grooved end, from styreneacrylonitrile copolymer. The caps were hemispherical, 5.6 mm in diameter, with a 0.8 mm diameter diametrical bore. Hemispherical overcaps had a 6.5 mm O.D., were 4.3 mm in length with the bottom hemispherically recessed to a depth of 1.3 mm, had a 0.8 mm diameter diametrical bore through the length of the overcap, and were injection molded from ethylenevinyl-acetate copolymer. The overcaps were pressed onto the 3 mm grooved extension of the tube.

Modifications of the above described dispensers that are obvious to those of skill in the mechanical, chemical, and other related arts are intended to be within the scope of the following claims.

What is claimed is:

1. In an osmotically driven fluid dispenser comprising an inner flexible bag adapted to contain the fluid, an intermediate layer of an osmotically effective solute composition at least partly encapsulating the bag, an outer, shape-retaining membrane encapsulating the layer of osmotically effective solute composition, said membrane being at least in part permeable to water, and a port that extends from the interior of the bag to the exterior of the dispenser through which the fluid may be charged into the bag and dispensed from the bag, the improvement wherein the layer of the osmotically effective solute composition is in the form of a thermoformed sleeve consisting essentially of a dispersion of about 50% to about 90% by weight osmotically effective solute, in about 10% to about 50% by weight water soluble thermoplastic polymer vehicle.

2. The improvement of claim 1 wherein the osmotically effective solute constitutes about 60% to about 70% by weight of the dispersion and the polymer vehicle constitutes about 30% to about 40% by weight of the dispersion.

3. The improvement of claim 1 wherein the polymer vehicle consists essentially of about 40% to about 70% by weight poly(ethylene oxide) having a molecular weight in the range of about 100,000 to about 4,000,000 and about 30% to about 60% by weight poly(ethylene glycol) having a molecular weight in the range of about 1,000 to about 30,000.

4. The improvement of claim 1 wherein the osmotically effective solute is sodium chloride and the vehicle consists of a mixture of poly(etyhlene oxide) of about 600,000 molecular weight, poly(ethylene glycol) of about 20,000 molecular weight, and colloidal silicon dioxide.

5. In an osmotically driven fluid dispenser comprising an inner flexible bag adapted to contain the fluid, an intermediate layer of an osmotically effective solute composition at least partly encapsulating the bag, an outer, shape-retaining membrane encapsulating the layer of osmotically effective solute composition, said membrane being at least in part permeable to water, and a port that extends form the interior of the bag to the exterior of the dispenser through which the fluid may be charged into the bag and dispensed from the bag, the improvement wherein the layer of the osmotically effective solute composition is in the form of a thermoformed sleeve consisting of a mixture of 64.5% by weight sodium chloride, 20% by weight poly(ethylene oxide) having a molecular weight of about 600,000, 15% by weight poly(ethylene glycol) having a molecular weight of about 20,000 and 0.5% by weight colloidal silicon dioxide.

* * * * *